United States Patent [19]

Weigele et al.

[11] 4,096,321
[45] Jun. 20, 1978

[54] PROCESS TO PRODUCE OXAZINOMYCIN AND INTERMEDIATES

[75] Inventors: Manfred Weigele, North Caldwell; Silvano DeBernardo, Upper Montclair, both of N.J.

[73] Assignee: Hoffmann-La Roche Inc., Nutley, N.J.

[21] Appl. No.: 743,887

[22] Filed: Nov. 22, 1976

[51] Int. Cl.² ..................... C07H 15/04; C07H 23/00
[52] U.S. Cl. ........................................ 536/120; 536/1; 536/121; 260/307 R; 260/340.9 R; 544/96
[58] Field of Search ................. 260/340.9 R; 536/120, 536/121

[56] References Cited

U.S. PATENT DOCUMENTS 4,043,937  8/1977  Kiss et al. ............... 260/340.9 X

FOREIGN PATENT DOCUMENTS 45-27,821  11/1970  Japan ............................. 536/120

Primary Examiner—Ethel G. Love
Attorney, Agent, or Firm—Samuel L. Welt; George M. Gould; Frank P. Hoffman

[57] ABSTRACT

A novel synthetic process to produce the antibiotic oxazinomycin is presented along with novel intermediates utilized in said process.

18 Claims, No Drawings

PROCESS TO PRODUCE OXAZINOMYCIN AND INTERMEDIATES

BACKGROUND OF THE INVENTION

The present invention involves a synthetic process to produce the known antibiotic oxazinomycin. Oxazinomycin also known as minimycin is a known C-nucleoside antibiotic, see, for example, T. Haneishi et al., J. Antibiotics, 24, 797 (1971) and K. Sosaki et al., J. Antibiotics, 25, 151 (1972). The antibiotic is known to be produced by several species of Streptomyces when utilized in a fermentation, see, for example, the above references and also Gutowski et al., Ann. N.Y. Acad. Sci., 255, 544 (1975). The antibiotic inhibits growth of both gram positive and gram negative bacteria and has demonstrated activity against transplantable tumors.

The starting material for the novel process is a compound of the formula

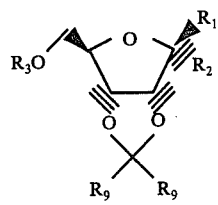

II wherein $R_1$ and $R_2$ are hydrogen or hydroxy but are different and $R_3$ is a group of the formula

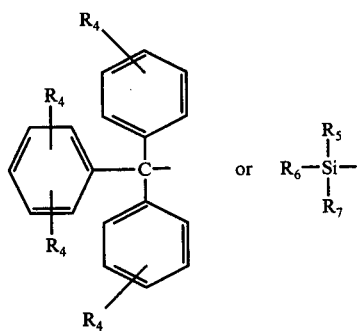

wherein $R_4$ is hydrogen, lower alkyl, lower alkoxy, halo or nitro and $R_5$, $R_6$ and $R_7$ are lower alkyl and $R_9$ is hydrogen or lower alkyl and is the same.

The starting material of formula II wherein $R_3$ is a trityl moiety, i.e.

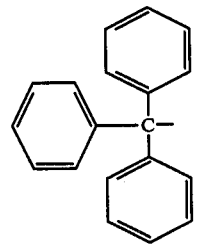

is known; see, for example, H. Ohrui et al., Tetrahedron Lett., 1951, (1973). The starting material of formula II wherein the trityl moiety is substituted may be made in an analogous manner as that disclosed in the Ohrui et al. reference. The novel process of the present invention is set forth in the following reaction scheme:

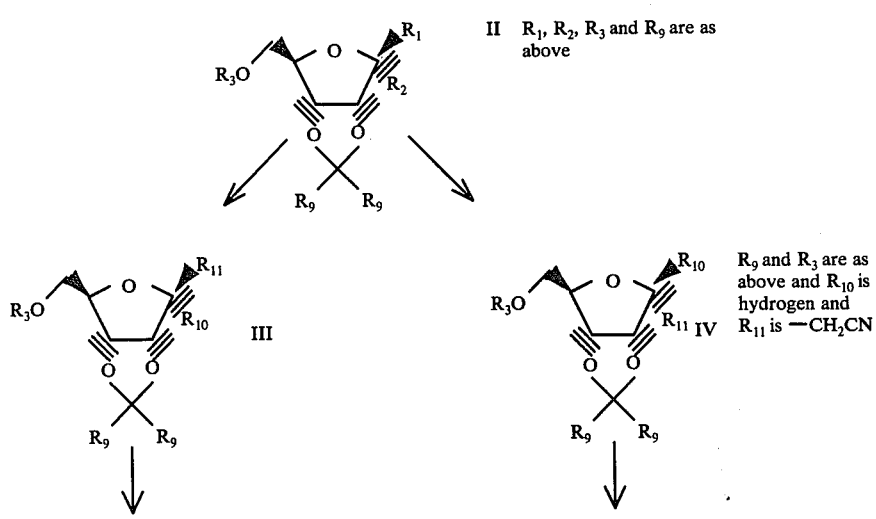

-continued
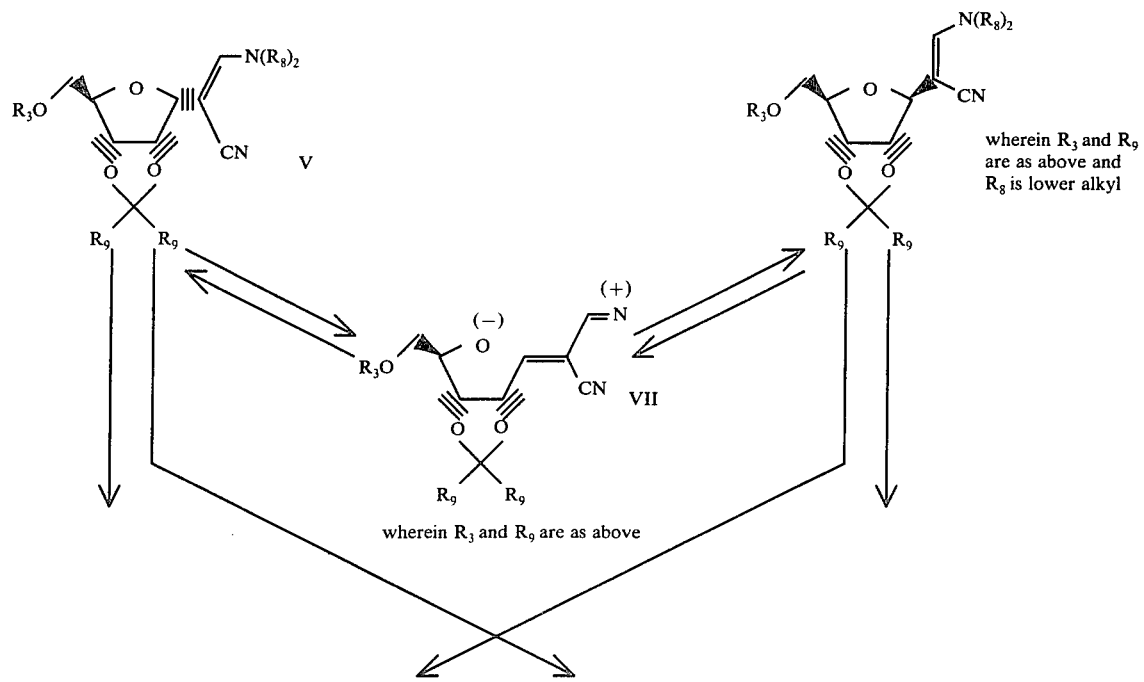
wherein $R_3$ and $R_9$ are as above and $R_8$ is lower alkyl
wherein $R_3$ and $R_9$ are as above
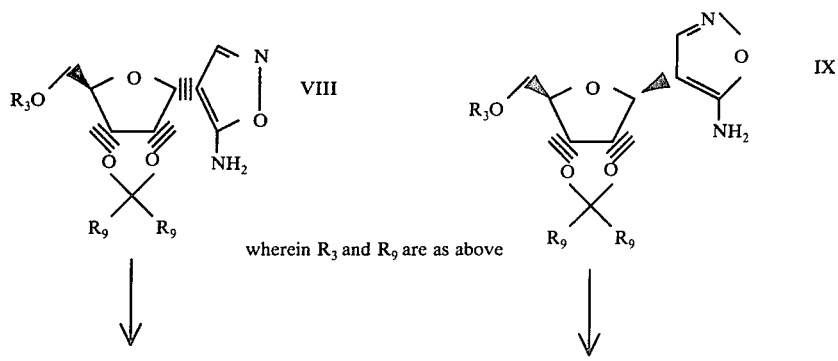
wherein $R_3$ and $R_9$ are as above
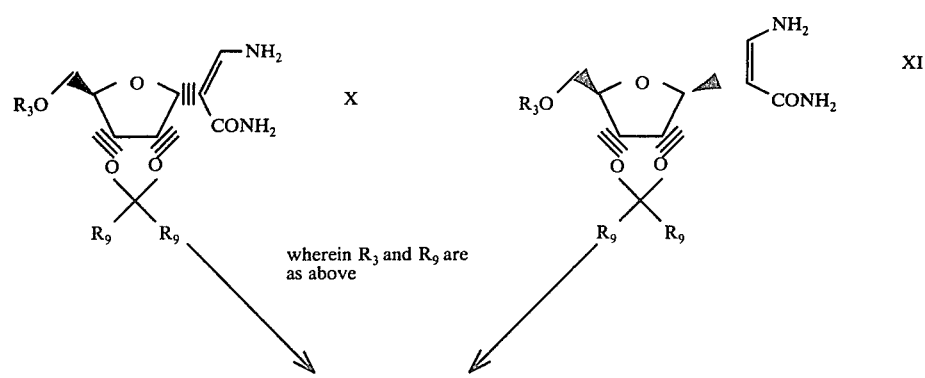
wherein $R_3$ and $R_9$ are as above

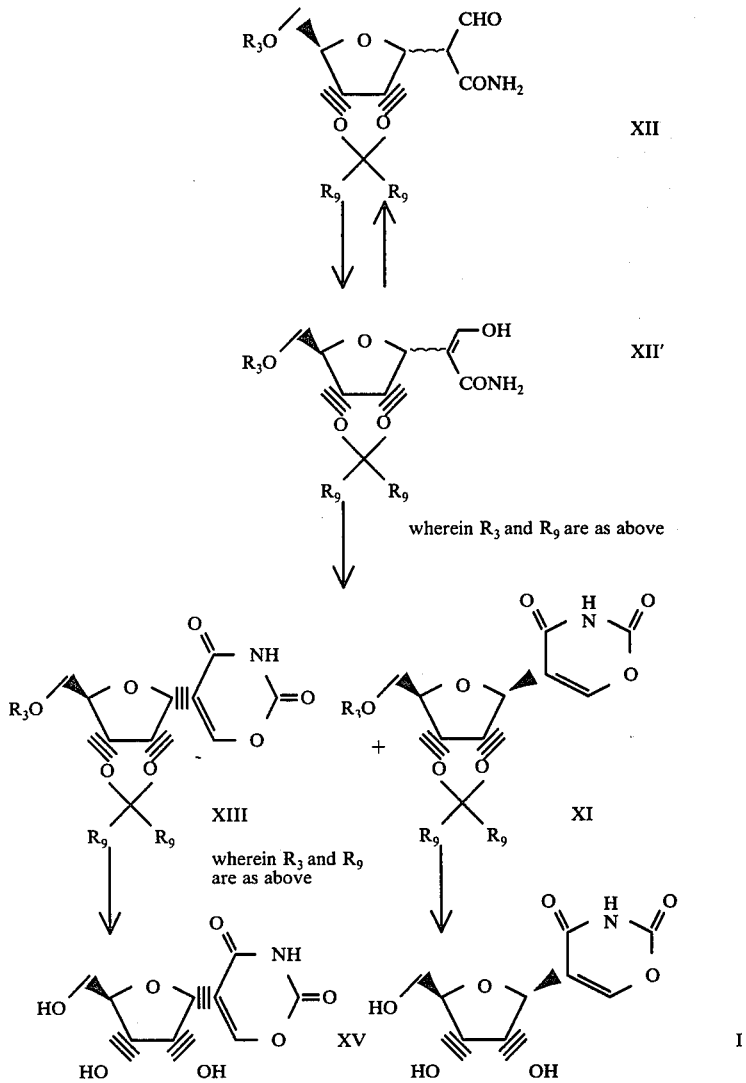

wherein R₃ and R₉ are as above wherein R₃ and R₉ are as above

II → III and IV

The starting material of formula II, i.e. a 2,3-O-alkylidene-5-O-R₃ -D-ribose is subjected to a Horner reaction with an alkali metal dialkyl cyanomethylphosphonate, such as a potassium or sodium diethyl cyanomethylphosphonate, in an inert organic solvent, such as, benzene or dimethoxyethane. The reaction is carried out at a temperature range of about 0°–40° C, preferably at room temperature. The epimeric ribosylocetonitriles of the formulas III and IV are found as a mixture in an approximate ratio of 1:2.

III and IV → V and VI

The epimeric ribosylacetonitriles of formulas III and IV are thereafter reacted with an aminal ester or an acetal of dimethylformamide, such as for example, bis (dimethylamino)-t-butyloxymethane at a temperature of from about room temperature to about 80° C, with room temperature preferred. The above formulated reaction results in a mixture of epimeric 2-(1'-ribosyl)-3-dialkylaminoacrylonitriles (2:1) of the formulas V and VI. Epimerization occurs readily between the compounds of formulas V and VI via opening and reclosure of the furanose ring. The compound of formula VII is thus a dipolar intermediate in the epimerization of these enamines.

V and VI → VIII and IX

The enamines of formulas V and VI are thereafter reacted with hydroxylamine in a polar solvent such as dimethylformamide at a temperature from about 50° C to 80° C, preferably at 65° C, to obtain the aminoisoxazoles of formulas VIII and IX.

VIII and IX → X and XI

The aminoisoxazoles of formulas VIII and IX are thereafter catalytically hydrogenated utilizing a noble metal catalyst such as platinum or palladium in an inert organic solvent, such as dimethoxyethane to yield the aminoacrylamides of formulas X and XI.

X and XI → XII ⇌ XII'

The aminoacrylamides of formulas X and XI thereafter are subjected to hydrolysis of the primary enamine function. Hydrolysis is effected under mild acidic conditions preferably in a two-phase system consisting of a 0.05N aqueous mineral acid, e.g., hydrochloric acid, and a non-water miscible organic solvent, such as chloroform or ethyl acetate. The resulting 2-(1'-ribofuranosyl)-2-formylacetamide is a mixture of aldehyde/enol tautomers as well as of C-1'-epimers of the formulas XII and XII'.

XII and XII' → XIII and XIV

The mixture of tautomers of formulas XII and XII' is thereafter reacted with N,N'-carbonyldiimidazole in an inert solvent, such as dimethoxyethane or benzene, in the presence of a catalytic amount of a base, such as an alkali metal hydride, e.g. sodium hydride to produce the epimers of formulas XIII and XIV. The epimeric mixture is distributed between water and in immiscible organic solvent. Separation between XIII and XIV is accomplished by techniques well known to the art, i.e. by chromatography.

XIII and XIV → XV and I

The epimers of formulas XIII and XIV are thereafter treated in acidic media, e.g., 90% trifluoroacetic acid to remove by hydrolysis the protecting groups $R_3$ and $>C(R_9)_2$ to afford the novel 1'-α-epimer of oxazinomycin (XV) and the known end product oxazinomycin (I).

As used in this disclosure, the term "lower alkyl" or "alkyl" comprehends both straight chain and branched chain ($C_1$-$C_7$) hydrocarbon radicals, preferably $C_1$-$C_4$ hydrocarbon radicals such as methyl, ethyl, propyl, isopropyl, t-butyl and the like.

By the term "alkoxy" is meant straight or branched chain saturated hydrocarbonoxy group containing from 1 to 7 carbon atoms, preferably from 1 to 4 carbon atoms, such as methoxy, ethoxy, propoxy and the like.

The term "halogen" or "halo" is used to include all four forms thereof, i.e., chlorine, bromine, fluorine and iodine.

The compound of formula XV is a novel compound having activity against Streptococci. It is therefore useful in wash solutions for sanitary purposes as in the washing of hands and the cleaning of equipment, floors or furnishings of contaminated rooms or laboratories.

EXAMPLE 1

2',3'-O-Isopropylidene-5'-O-trityl-d-ribofuranosylacetonitrile

To a suspension of 2.00 g (83.3 mmol) of NaH in 300 ml of dry DME (stirred under argon) was added dropwise (over 30 min) 17 ml (107.7 mmol) of diethyl cyanomethylphosphonate while cooling in an ice-water bath. After evolution of $H_2$ had ceased, the cooling was discontinued and 30 g of 2,3-O-isopropylidene 5-O-trityl-d-ribose[1] (69.36 mmol) in 200 ml of dry DME was added to the clear solution within 30 min. The reaction mixture was maintained for 2 hr at room temperature under argon. It was then distributed between 2 l. of $Et_2O$ and 1 l. of $H_2O$. The aqueous layer was extracted with 1 l. of $Et_2O$. The combined extracts were washed to neutrality with half-saturated brine (2 × 500 ml), diluted with benzene (500 ml), dried ($Na_2SO_4$), and evaporated to dryness in vacuo. The residual oil was dissolved in 40 ml of AcOEt-cyclohexane 1:4 and the solution chromatographed on a column (105 × 6 cm) containing 1.15 kg of silica gel. The column was developed with 5 l. of AcOEt-cyclohexane, 1:4.

[1]H. Ohrui, J. J. Fox, Tetrahedron Lett., 195 (1973).

Early fractions afforded crystalline 2,3-O-isopropylidene-5-O-trityl-α-d-ribofuranosyl acetonitrile, mp 130°, from MeOH, $[\alpha]^{25}$ d 10.1° (c 0.9982, $CHCl_3$) (reported[10] 9.8°). Further elution gave 2,3-O-isopropylidene-5-O-trityl-β-d-ribofuranosyl acetonitrile, contaminated with a minor amount of the α-epimer and finally pure β-epimer as a colorless syrup. EXAMPLE 2

3-Dimethylamino-2-(2',3'-O-isopropylidene-5'-O-trityl-d-ribosyl)-acrylonitrile A mixture (2:3) of the α and β-epimers of Example 1 (30.5 g, 67 mmol) was dissolved in 250 ml of dry DMF and the solution was placed in a 500 ml flask fitted with a reflux condenser. An excess of bis(dimethylamino)-t-butoxymethane[2] (45 ml) was added in one portion and the reaction mixture was stirred under argon for 3 hrs at 55°. The excess aminal ester and most of the solvent were evaporated in vacuo at 50°. The remaining dark syrup was taken up in $CHCl_3$ (ca. 30 ml) and the solution applied to a column containing 400 g of silica gel. The column was developed with $CHCl_3$ (200 ml) and $CHCl_3$—MeOH, 99.5:0.5 (2500 ml), the eluate being monitored by tlc ($CHCl_3$—MeOH, 98:2).

Fractions containing the final epimers were pooled. After evaporation of the solvents, the residue was dissolved in $CHCl_3$ (ca. 40 ml); dilution with $Et_2O$ (300 ml) in portions yielded, after cooling, crystalline 3-dimethylamino-2-(2',3'-O-isopropylidene-5'-O-trityl-α-d-ribosyl)acrylonitrile. Mother liquors and washings ($Et_2O$) were evaporated in vacuo. The light brown residue, dried at 50°/0.01 mm Hg, was purified by chromatography on 540 g of silica gel. The column, packed in $CHCl_3$, was eluted with $CHCl_3$—MeOH, 99:1 (1500 ml) and 98:2 (3000 ml). The oil obtained from the early fractions was taken up in $Et_2O$. Upon concentration of the solution to ca. 25 ml, dilution with cyclohexane (60 ml) in portions, and cooling, pure 3-dimethylamino-2-(2',3'-O-isopropylidene-5'-O-trityl-β-D-ribosyl) acrylonitrile 6 was obtained (as a solvate with one mole of cyclohexane).

Later fractions contained an epimeric mixture. Fractional crystallization of the residue gave additional α-epimer from $CHCl_3$-$Et_2O$, then an additional amount of solvated β-epimer from $ET_2O$-chclohexane. A further amount of crystalline β-epimer could be isolated by chromatography of the mother liquors on 400 g of silica gel in AcOEt-cyclohexane 3:7. The α epimer had mp 180°–181.5°, $[\alpha]^{25}D-51.8°$ (c. 0.9.856, $CHCl_3$); uv (EtOH) infl. 230 nm (ε 11,500), max 276 (16,900); ir ($CHCl_3$) 2180, 1634, 1107, 1074, 708 $cm^{-1}$; NMR ($CDCl_3$) δ 1.33 and 1.56 (2s, C($CH_3$)$_2$), 3.11 (s, N($CH_3$)$_2$), 3.20 (ddd, $CH_2$OTr), 4.22 (t, H-4'), 4.64 (ed, H-1' and H-3'), 6.61 (s, vinylic), 7.20–7.55 (m, 15, arom.)

Anal. Calcd for $C_{32}H_{34}N_2O_4$: C, 75.27; H, 6.71; N, 5.49. Found: C, 75.11; H, 6.46; N, 5.50.

The β-epimer had mp 78°–83°, $[\alpha]^{25}D-28.7°$ (c 0.9917, $CHCl_3$); uv (EtOH) infl. 230 nm (ε 11,500), max 274/5 (18,200); ir ($CHCl_3$) 2815, 2190, 1637, 1075, 708 $cm^{-1}$; NMR ($CDCl_3$) δ 1.32 and 1.53 (2s, C($CH_3$)$_2$), 3.06 (s, N($CH_3$)$_2$), 3.28 (d, O$CH_2$Tr), 4.05 (q, H-4', J = 4 Hz), 4.15 (d, H-1', J = 5 Hz), 4.51 (dd, H-3'), 4.66 (dd, H-2'), 6.55 (s, vinylic), 7.20–7.60 (m, 15, arom.).

Anal. Calcd for $C_{32}H_{34}N_2O_4 \cdot C_6H_{12}$: C, 76.74; H, 7.80; N, 4.71. Found: C, 76.81; H, 8.14; N, 4.79.

EXAMPLE 3

5-Amino-4-(2',3'-O-isopropylidene-5'-O-trityl-D-ribosyl)isoxazole

A mixture (2:1) of α and β epimers of Example 2 (30.69 g, 57-34 mmol) was dissolved in 300 ml of dry DMF. To this solution was added 50 ml of dry pyridine and 5.10 g (73.3 mmol) of $NH_2OH \cdot HCl$. Upon stirring at 68°–70° under argon, a clear solution was obtained within 15 min. The reaction was kept at 70° for 6.5 hrs while monitoring by tlc ($Et_2O$-cyclohexane, 10:3). Then the solvents were evaporated in vacuo at 45° and the residual syrup was distributed between $CHCl_3$ (1200 ml) and $H_2O$ (600 ml). The aqueous layer was extracted with a second portion of $CHCl_3$ (600 ml). The organic extracts were combined, washed with half-saturated brine (3 × 400 ml), dried ($Na_2SO_4$) and evaporated in vacuo. The residual syrup was chromatographed on 400 g of silica gel, successively with $CHCl_3$—MeOH, 98.5:1.5 (900 ml) and 98:2 (1500 ml). Early fractions were rechromatographed on 600 g silica gel ($CHCl_3$—MeOH, 98:2, 3500 ml) to give unreacted starting material, crystalline 5-amino-4-(2',3'-O-isopropylidene-5'-O-trityl-β-D-ribosyl)isoxazole (from $Et_2O$-petroleum ether 30°–60°) as a solvate with 1 mole of $Et_2O$, and 5-amino-4-(2',3'-O-isopropylidene-5'-O-trityl-α-D-ribosyl)-isoxazole as an amorphous foam.

The pure α-epimer had $[\alpha]^{25}D$ −11.5° (c, 0.9960, $CHCl_3$); uv (EtOH) max 247 nm (δ 80000; ir ($CHCl_3$) 3490, 3390, 1646, 1505, 1495, 1105, 1074, 706 $cm^{-1}$; NMR (DMSO-$d_6$) δ 1.24, 1.44 (2s, C(C$\underline{H}_3$)$_2$), 3.10 (m, C$\underline{H}_2$OTr), 4.06 (t, H-4'), 4.54 (q, H-2'), 4.62 (d, H-3'), 4.72 (d, H-1', (d, H-1'), 6.54 (broad s, exchangeable, N$\underline{H}_2$), 7.20–7.50 (m, 15 aromatic), 8.01 (s, =CH—).

Anal. Calcd for $C_{30}H_{30}N_2O_5$: C, 72.27; H, 6.07; N, 5.61. Found: C, 71.49; H, 6.07; N, 5.67.

The pure β-epimer, a solvate with 1 mole of $ET_2O$, had mp 90°–96°; $[\alpha]^{25}D$ −13.4° (c 0.9890, $CHCl_3$); uv (EtOH) max 248nm (ε 8400); ir 3485, 3370, 1653, 1514, 1505 (w), 1080, 707 $cm^{-1}$; NMR (DMSO-$d_6$) δ1.09 (t, $CH_3$ of $ET_2$), 1.27, 1.49 (2s, C(CH$_3$)$_2$); 3.13 (d, $CH_2$OTr), 3.37 (q, C$\underline{H}_2$ of $Et_2O$), 3.96 (q, H-4'), 4.50-4.78 (m, H-3', H-2', H-1'), 6.78 (broad s, —N$\underline{H}_2$), 7.16–7.52 (m, 15 aromatic), 8.10 (s, =C$\underline{H}$—).

Anal. Calcd for $C_{30}H_{30}N_2O_5 \cdot C_4H_{10}O$: C, 71.31; H, 7.04; N, 4.89. Found: C, 71.29; H, 7.15; N, 4.84.

EXAMPLE 4

3-Amino-2-(2',3'-O-isopropylidene-5'-O-trityl-α-D-ribosyl)-acrylamide

A solution of 5.01 g (10.05 mmol) of the α-epimer of Example 3 in 75 ml of dry DME was hydrogenated at room temperature in the presence of 250 mg of $PtO_2$. The consumption of $H_2$ was 285 ml within 25 min (theor. 274 ml). The mixture was stirred under nitrogen with a small amount of decolorizing carbon and filtered through a pad of Celite. After evaporation of the solvents in vacuo at <30°, the residue was taken up in 250 ml of $CHCl_3$. The solution was washed with 2 × 200 ml of $H_2O$, dried ($Na_2SO_4$), and evaporated under reduced pressure. Upon drying at 0.005 mmHg at room temperature for 2 days and at 50° for 2 hrs, the final product was obtained as a white foam; $[\alpha]^{25}D$ -27.2 (c 0.8655, $CHCl_3$); uv (EtOH) max. 271 nm (ε10,000); ir ($CHCl_3$) 3510, 3375, 1660, 1576, 1100, 1070, 705 $cm^{-1}$; NMR (DMSO-$d_6$) δ 1.18, 1.34 (2s, C(C$\underline{H}_3$)$_2$), 2.80–3.25 (m, C$\underline{H}_2$OTr), 4.03 (t, H-4'), 4.32–4.64 (m, H-1', H-2', H-3'), 6.20 (broad s, NH$_2$), 6.72 (t, =C$\underline{H}$-; s, upon $D_2O$ exch.), 7.00-7.64 (m, ~15 aromatic and N$\underline{H}_2$, exch.), 8.24 ($CHCl_3$).

Anal. Calcd for $C_{30}H_{32}N_2O_5 \cdot 0.65CHCl_3$: C, 63.67; H, 5.69; N, 4.85. Found: C, 63.83; H, 5.80; N, 4.53.

EXAMPLE 5

3-Amino-2-(2', 3'-O-isopropylidene-5'-O-trityl-β-D-ribosyl)-acrylamide was prepared analogously by hydrogenation of the β-epimer of Example 3. White foam from $CHCl_3$, $[\alpha]^{25}D$ −12.7° (c 0.8694, $CHCl_3$); uv (EtOH) max 272 nm ( 12,100); ir ($CHCl_3$) 3510, 3485, 3355, 1665, 1580, 1100, 706 $cm^{-1}$; NMR (DMSO-$d_6$) 1.26, 1.46 (2s, C(C$\underline{H}_3$)$_2$), 3.21 (m, C$\underline{H}_2$OTr), 3.87 (q, H-4'), 4.14 (q, H-2' or H-3'), 4.60 (m, H-1' and H-2' or H-3'), 6.26 (broad s, N$\underline{H}_2$, exch.), 6.81 (t, =C$\underline{H}$-, collapses slowly to a s upon $D_2O$ exch.), 7.10–7.55 (m, 15 aromatic and N$\underline{H}_2$), 8.29 ($CHCl_3$).

Anal. Calcd for $C_{30}H_{32}N_2O_5 \cdot 0.65$ $CHCl_3$: C, 63.67; H, 5.69; N, 4.85. Found: C, 63.99; H, 5.93; N, 4.67.

EXAMPLE 6

2-Formyl-2-(2', 3'-O-isopropylidene-5'-O-trityl-D-ribosyl)acetamide

A solution of the product of Example 4 (or 5) (4.218g) in 250 ml of $CHCl_3$, was vigorously stirred for 7 hrs at room temperature together with 500 ml of 0.05N HCl. Then 250 ml of $CHCl_3$ was added and the layers were separated. The aqueous phase was extracted with 250 ml of $CHCl_3$. The combined extracts were washed with 3 × 300 ml of $H_2O$, dried ($Na_2SO_4$), and evaporated in vacuo at ≦35°. The residue was dissolved in 10 ml of AcOEt-$Et_2O$, 1:1, and the solution was chromatographed on 400 g of silica gel with AcOEt-$Et_2O$, 35:65 (2500 ml). The residue obtained from the first fractions was enriched in the α-epimers (α/β approx. 2:1, as determined by integration of the CHO protons in NMR), while the subsequent eluate gave a white foam in which the β epimers were largely predominant (α/β ca. 2:9). This material was used in the next step without any further purification.

Both fractions had very similar spectral properties; uv (EtOH) max 266 nm (ε 2600); (0.1N KOH) sh 230 nm (9600), max 270 (12,300); ir ($CHCl_3$) 3480, 3345, 1710 (wk), 1655 $cm^{-1}$; (pyridine) 1728, 1690, 1658 $cm^{-3}$; NMR (partial, DMSO-$d_6$) ε 4.07 (q, H-4' of β epimers), 4.33 (t, H-4' of α epimers), 9.58-9.72 (m, C$\underline{H}$O, integration for less than one proton, indicating presence of tautomeric forms).

EXAMPLE 7

5-(2',3'-O-Isopropylidene-5'-O-trityl-D-ribosyl)-1,3-oxazin-2,4-dione α & β-epimers To a stirred suspension of 353 mg of KH (22.5% in oil, 2 mmol) in 20 ml of dry DME was added dropwise at 10° a solution of 2.48 g (4.94 mmol) of the product of Example 6 in 25 ml DME. After evolution of $H_2$ had ceased, 1.62 g (10 mmol) of 1,1'-carbonyldimidazole dissolved in 35 ml of DME was added dropwise at 10° to the clear solution. The reaction mixture was stirred under argon at room temperature for 6 hours. It was then diluted with 500 ml of $Et_2O$ and 175 ml of cold 0.15N HCl. The aqueous layer was extracted with a second portion of $Et_2O$. The organic extracts were washed with $H_2O$ (4 × 100 ml), diluted with 150 ml of benzene, dried ($Na_2SO_4$), and evaporated at 35° under reduced pressure. The residue was dissolved in 8 ml of AcOEt-$Et_2O$, 35:65, and the solution chromatographed on 400 g of silica gel with 2000 ml of the same solvent mixture. Epimeric 5-(2',3'-O-isopropylidene-5'-O-trityl-D-ribosyl)-1,3-oxazin-2,4-dione was eluted first. Starting material was recovered from later fractions.

Partial separation of the epimers was achieved by column chromatography. Thus, 3.20 g of a mixture the final epimers was dissolved in 10 ml of AcOEt-Et$_2$O-cyclohexane 30:10:60 and the solution applied to a column (80 × 4.6 cm) packed with 600 g of silica gel. Elution with AcOEt-Et$_2$O-cyclohexane, 30:10:60 (4000 ml, 1.5 ml/min) afforded the less polar 5-(2',3'-O-isopropylidene-5'-O-trityl-α-D-ribosyl)-1,3-oxazin-2,4-dione as an amorphous white powder, which after evaporation from AcOEt-n-heptane and drying at 70°/0.005 mmHg for 24 hrs had: [α]$^{25}$D −48.4° (c 1.0015, CHCl$_3$); uv (EtOH) infl. 230 nm (ε 12,700), 259 (980), 270 (480); ir (CHCl$_3$) 3390, 1790, 1757, 1725, 1705, 1080, 708 cm$^{-1}$; NMR (DMSO-d$_6$) δ1.23, 1.33 (2s, C(CH$_3$)$_2$), 3.16 (d, CH$_2$OTr), 4.19 (t, H-4'), 4.66 (d, H-3'), 4.87 (t, H-2'), 4.93 (d, H-1'), 7.20–7.50 (m, 15 aromatic), 7.64 (s, =CH—), 12.02 (s, exch., NH).

Anal. Calcd for C$_{31}$H$_{29}$NO$_7$: C, 70.58; H, 5.54; N, 2.65. Found: C, 70.59; H, 5.49; N, 2.71.

The residue obtained from the remaining fractions could be resolved into its components by preparative high pressure liquid chromatography. Thus, batches of ca. 500 mg of the mixture were chromatographed on an 8 ft. × ⅜ in. column packed with Porasil A, using AcOEt-N-heptane, 1:4, as the eluent. Two recycles provided complete separation of the epimers. After evaporation of the fractions in vacuo, the residues were dried at 70°/0.005 mmHg for 24 hrs to give the α-epimer and 5-(2',3'-O-isopropylidene-5'-O-trityl-β-D-ribosyl)-1,3-oxazin-2,4-dione as a white amorphous powder: [α]$^{25}$D 8.4° (c 0.9912, CHCl$_3$); uv (EtOH) infl. 230 nm (ε 13,400), 260 (950), 270 (450); ir (CHCl$_3$) 3390, 1790, 1760, 1725, 1085, 710 cm$^{-1}$; NMR (DMSO-d$_6$) δ 1.25, 1.47 (2s, C(CH$_3$)$_2$), 3.13 (d, CH$_2$OTr), 4.03 (q, H-4'), 4.55 (t, H-3'), 4.64–4.83 (m, H-1', H-2'), 7.20–7.50 (m, 15 aromatic), 7.79 (s, =CH—), 12.01 (s, exch., NH).

Anal. Calcd for C$_{31}$H$_{29}$NO$_7$: C, 70.58; H, 5.54; N, 2.66. Found: C, 70.63; H, 5.72; N, 2.66

EXAMPLE 8

5-α-D-Ribofuranosyl-1,3-oxazin-2,4-dione

A solution of 791 mg (1.50 mmol) of the α-epimer of Example 7 in 25 ml of 90% CF$_3$COOH was stirred at room temperature for 2.5 hrs. The solvents were removed at ca. 30°/0.2 mmHg and the residue was dried azeotropically by evaporation from abs. EtOH. The resulting solution was triturated with 25 ml of benzene and the suspension stirred at room temperature for 1 hr. The insoluble was collected by filtration and washed with several small portions of Et$_2$O to give the final product as a white crystalline powder, mp 163°–167°, dec. (with previous softening), pure by tlc.

Recrystallization from a small volume of MeOH-H$_2$O (5:1) afforded 250 mg of needles, mp 168°–170°; [α]$^{25}$D −82.6 (c 0.9918, H$_2$O); uv max (H$_2$O) 230 nm (ε 4420); ir (KBr) 3400, 3320, 1795, 1770, 1690, 1675, 1653 cm$^{-1}$; NMR (D$_2$O) δ 3.74, 3.97 (CH$_2$, 2dd, J$_{vic}$ 2.5, 5, J$_{gem}$ 12.5 Hz), 4.04 (H-4', ddd, J 2.5, 5, 7.5 Hz), 4.33 (H-3', dd, J 4, 7.5 Hz), 4.46 (H-2', dd, J 4, 3 Hz), 5.12 (H-1', dd, J 3, 1.5 Hz), 7.77 (vinylic, d, J 1.5 Hz); ms (m/e) 245 (M$^+$), 227 (M—H$_2$O), 201 (M—CO$_2$), 184 (M—HNCO), 140, 112.

Anal. Calcd. for C$_9$H$_{11}$NO$_7$: C, 44.09; H, 4.52; N, 5.71. Found: C, 43.98; H, 4.40; N, 5.58.

EXAMPLE 9

5-β-D-Ribofuranosyl-1,3-oxazin-2,4-dione (Oxazinomycin)

A solution of 1.298 g (2.46 mmol) of the β-epimer of Example 7 in 35 ml of 90% CF$_3$COOH was stirred at room temperature for 3 hrs. The solvents were removed at ca. 30°/0.2 mmHg. The residue was dried azeotropically by evaporation from absolute EtOH and purified by chromatography on 200 g of silica gel. The column was developed with AcOEt—AcMe—MeOH—H$_2$O, 70:10:5:5, and appropriate fractions were evaporated in vacuo at 30°. Crystallization of the residue from MeOH containing a small amount of H$_2$O, afforded oxazinomycin, mp 153°–155°. The mother liquors, after evaporation, gave an additional yield from AcMe, mp 152°–154°. Mixture mp with an authentic sample: 153°–155°. Occasionally, upon slow recrystallization from water/methanol, a second polymorph was obtained, which had mp 161°–162°, dec. (reported $^{4-6}$ 161°). Synthetic and natural oxazinomycin had identical r$_f$-values in several tlc systems; e.g. in EtOAC:AcMe:-MeOH:H$_2$O, 70:10:5:5, the r$_f$ was 0.34. [α]$^{25}$D + 15.29° (c 0.9942, H$_2$O); uv max (H$_2$O) 230 nm (ε 4700); ir (KCl) 3470, 3420, 1797, 1773, 1678 cm$^{-1}$; NMR (D$_2$O)δ 3.77, 3.90 (CH$_2$, 2dd, J$_{vic}$ 5,3, J$_{gem}$ 12.5 Hz), 4.06 (H-4', ddd, J 5,3,5 Hz), 4.19 (H-3', t, J 5,5 Hz), 4.34 (H-2', t, J 5, 5 Hz), 4.72 (H-1', d, J 5 Hz), 7.88 (vinylic, s); ms (m/e) 227 (M—H$_2$0), 209, 202, 196.

Anal. Calcd for C$_9$H$_{11}$NO$_7$: C, 44.09; H, 4.52; N, 5.71. Found: C, 44.22; H, 4.52; N, 5.70.

EXAMPLE 10

2,3O-isopropylidene-5-O-tert-butyldimethylsilyl-D-ribose

To 19.80g of 2,3-O-isopropylidene-D-ribofuranose (104.1 mmol) dissolved in 60 ml of dry pyridine, was added dropwise, while stirring at 0°–4°, a solution of 17.26 g (118.1 mmol) of tert-butyldimethylsilyl chloride in 80 ml of dry pyridine. The stirring was maintained for 30 min. in the ice-water bath, then for 6 hr. at room temperature. Most of the pyridine was then removed by evaporation under reduced pressure and the resulting slurry was distributed between ice cold H$_2$O (500 ml) and AcOEt (2×500 ml). The organic extracts were washed with 2×250 ml of semi-saturated NaCl solution, dried with Na$_2$SO$_4$, and evaporated in vacuo. The residual syrup was chromatographed on 600 g of silica gel 60 (0.063–0.200 mm). Elution with AcOEt-cyclohexane 3:7, evaporation of the pertinent fractions, and crystallization of the residue from cold (−40°) pentane afforded 2,3-O-isopropylidene-5O-tert-butyldimethylsilylβ-D-ribose, m.p. 52°–54°; [α]$_D$$^{25}$ −13.6° (c 1.0078, CHCl$_3$).

Anal. For C$_{14}$H$_{28}$O$_5$: Calcd. C55.24, H 9.27; Found: C 55.34, H 9.18.

Evaporation of the mother liquors afforded an additional amount of crystalline title compound as an epimeric mixture.

EXAMPLE 11

2,3-O-isopropylidene-5-O-tert-butyldimethylsilyl-D-ribosylacetonitrile

To a suspension of 333 mg (13.85 mmol) of NaH in 30 ml of dry 1,2-dimethoxyethane (DME), stirred under argon, was added dropwise 2.50 ml of diethyl cyanomethylphosphorane (15.45 mmol). To the resulting yellow solution was added 3.84 g of 2,3O-isopropylidene-5-O-tert-butyldimethylsilyl-β-D-ribose (12.61 mmol) dissolved in 30 ml of dry DME, over a period of 10 minutes. After stirring at room temperature for 2 hrs., the reaction was distributed between H₂O (250 ml) and Et₂O (2 × 500 ml). The organic extracts were washed to neutrality with H₂O (4 × 100 ml), diluted with cyclohexane, dried (Na₂SO₄), and evaporated to dryness in vacuo. Chromatography of the residual oil on 350 g of silica gel 60 (0.063–0.200 mm) usng AceEt - cyclohexane 1:4 as eluent afforded 2,3-O-isopropylidene-5-D-tert-butylmethylsilyl-α -D-ribofuranosylacetonitrile (colorless oil; $[\alpha]_D^{25}$ −17.3 (cl.1355, CHCl₃); Anal. For $C_{16}H_{29}HO_4Si$; Calcd.: C 58.68, H 8.93, N 4.28; Found: C 58.69, H 8.71, N 4.68), the epimeric mixture, and then 2,3-O-isopropylidene-5-O-tert-butyldimethylsilyl-β-d-ribosylacetonitrile (colorless oil; $[\alpha]_D^{25}$ −21.5 (cl 1.0315, CHCl₃); Anal. For $C_{16}H_{29}NO_4$ Calcd.: C 58.68, H 8.93, N 4.28; Found: C 58.75, H 9.01, N 4.23).

What is claimed is:

1. A compound of the formula

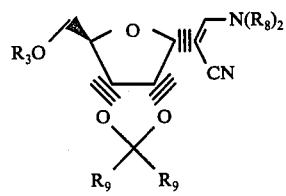

wherein $R_8$ is lower alkyl, $R_9$ is hydrogen or lower alkyl and $R_3$ is selected from the group consisting of

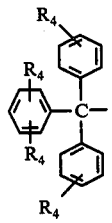

wherein $R_4$ is selected from the group consisting of hydrogen, lower alkyl, lower alkoxy, halo and nitro and

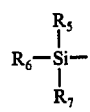

wherein $R_5$, $R_6$ and $R_7$ are lower alkyl.

2. A compound of the formula

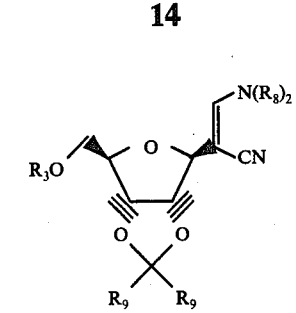

wherein $R_8$ is lower alkyl, $R_9$ is hydrogen or lower alkyl and $R_3$ is selected from the group consisting of

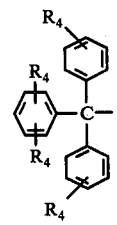

wherein $R_4$ is selected from the group consisting of hydrogen, lower alkyl, lower alkoxy, halo and nitro and

wherein $R_5$, $R_6$ and $R_7$ are lower alkyl.

3. A compound of the formula

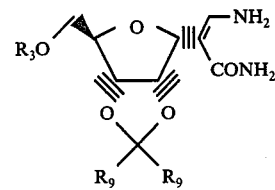

wherein $R_9$ is hydrogen or lower alkyl and $R_3$ is selected from the group consisting of

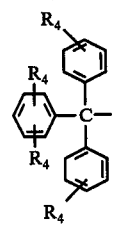

wherein $R_4$ is selected from the grup consisting of hydrogen, lower alkyl, lower alkoxy, halo and nitro and

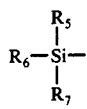

wherein $R_5$, $R_6$ and $R_7$ are lower alkyl.

4. A compound of the formula

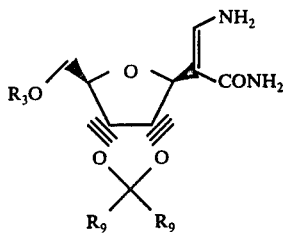

wherein $R_9$ is hydrogen or lower alkyl and $R_3$ is selected from the group consisting of

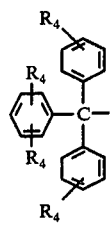

wherein $R_4$ is selected from the group consisting of hydrogen, lower alkyl, lower alkoxy, halo and nitro and

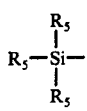

wherein $R_5$, $R_6$ and $R_7$ are lower alkyl.

5. A compound of the formula

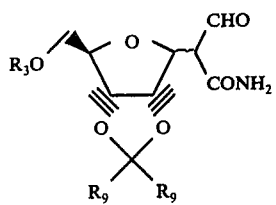

wherein $R_9$ is hydrogen or lower alkyl and $R_3$ is selected from the group consisting of

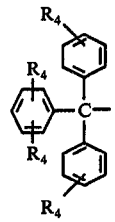

wherein $R_4$ is selected from the group consisting of hydrogen, lower alkyl, lower alkoxy, halo and nitro and

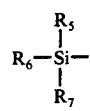

wherein $R_5$, $R_6$ and $R_7$ are lower alkyl.

6. A compound of the formula

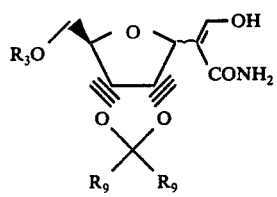

wherein $R_9$ is hydrogen or lower alkyl and $R_3$ is selected from the group consisting of

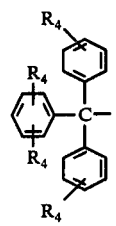

wherein $R_4$ is selected from the group consisting of hydrogen, lower alkyl, lower alkoxy, halo and nitro and

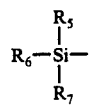

wherein $R_5$, $R_6$ and $R_7$ are lower alkyl.

7. A compound of the formula

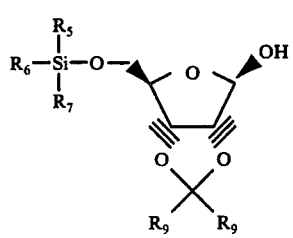

wherein $R_9$ is hydrogen or lower alkyl and $R_5$, $R_6$ and $R_7$ are lower alkyl.

8. The compound of claim 7 of the formula

9. A compound of the formula

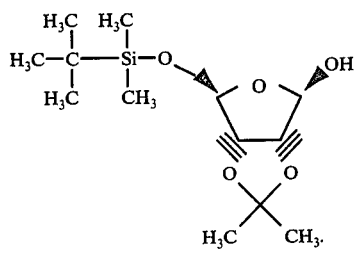

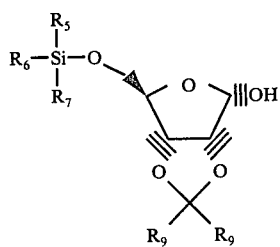

wherein $R_9$ is hydrogen or lower alkyl and $R_5$, $R_6$ and $R_7$ are lower alkyl.

10. The compound of claim 9 of the formula

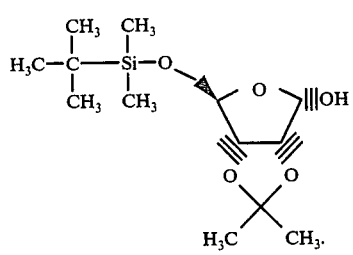

11. A compound of the formula

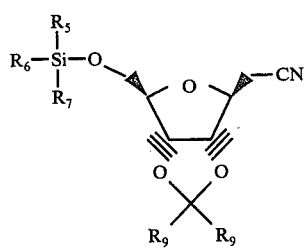

wherein $R_9$ is hydrogen or lower alkyl and $R_5$, $R_6$ and $R_7$ are lower alkyl.

12. The compound of claim 11 of the formula

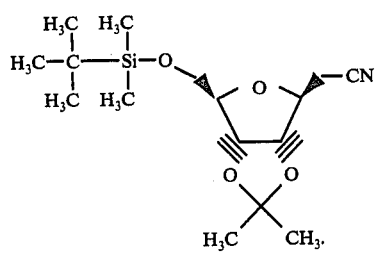

13. A compound of the formula

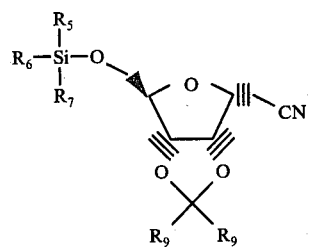

wherein $R_9$ is lower alkyl or hydrogen and $R_5$, $R_6$ and $R_7$ are lower alkyl.

14. The compound of claim 13 of the formula

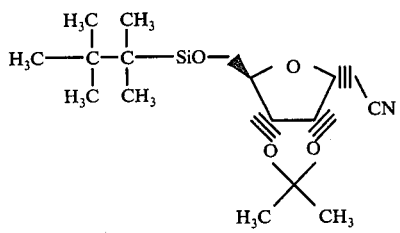

15. The compound of claim 1 wherein $R_3$ is

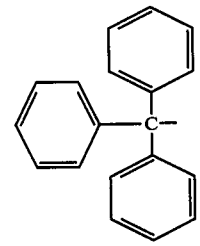

and
$R_8$ and $R_9$ are methyl.

16. The compound of claim 2 wherein $R_3$ is

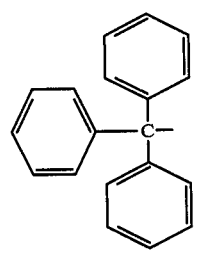

and
$R_8$ and $R_9$ are methyl.

17. The compound of claim 3 wherein $R_3$ is

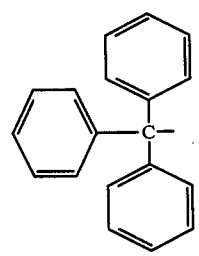

and
$R_9$ is methyl.
18. The compound of claim 4 wherein $R_3$ is
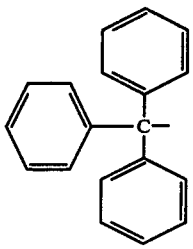
and
$R_9$ is methyl.

UNITED STATES PATENT AND TRADEMARK OFFICE
CERTIFICATE OF CORRECTION

PATENT NO. : 4,096,321
DATED : June 20, 1978
INVENTOR(S) : Manfred Weigele and Silvano DeBernardo It is certified that error appears in the above-identified patent and that said Letters Patent are hereby corrected as shown below:

Column 14, line 64, claim 3, "grup" should be: group

Column 15, line 40, claim 4

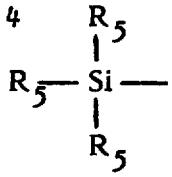

should be:

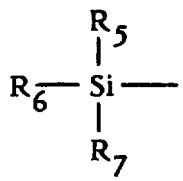

*Signed and Sealed this*

*Fifth* Day of *February 1980*

[SEAL]

Attest:

SIDNEY A. DIAMOND

*Attesting Officer*     *Commissioner of Patents and Trademarks*